(12) United States Patent
Jensen

(10) Patent No.: US 8,452,390 B2
(45) Date of Patent: May 28, 2013

(54) APPARATUS AND METHOD FOR BIOELECTRICAL IMPEDANCE MEASUREMENTS

(75) Inventor: Björn Jensen, Hamburg (DE)

(73) Assignee: Seca AG (CH)

( * ) Notice: Subject to any disclaimer, the term of this patent is extended or adjusted under 35 U.S.C. 154(b) by 257 days.

(21) Appl. No.: 12/896,540

(22) Filed: Oct. 1, 2010

(65) Prior Publication Data

US 2011/0245710 A1    Oct. 6, 2011

(30) Foreign Application Priority Data

Oct. 1, 2009   (EP) ..................................... 09171972

(51) Int. Cl.
*A61B 5/05*   (2006.01)
(52) U.S. Cl.
USPC .......................................................... 600/547
(58) Field of Classification Search
CPC ...... A61B 5/0537; A61B 5/053; A61B 5/4872; A61B 5/4869; A61B 5/0531
USPC .......................................................... 600/547
See application file for complete search history.

(56) References Cited

U.S. PATENT DOCUMENTS

| | | | |
|---|---|---|---|
| 5,335,667 A | 8/1994 | Cha et al. | |
| 5,720,296 A | 2/1998 | Cha | |
| 6,308,096 B1 * | 10/2001 | Masuo | 600/547 |
| 6,393,317 B1 | 5/2002 | Fukuda et al. | |
| 6,567,692 B1 | 5/2003 | Kohashi | |
| 6,714,813 B2 | 3/2004 | Ishigooka | |
| 7,313,435 B2 | 12/2007 | Nakada et al. | |
| 2005/0054944 A1 * | 3/2005 | Nakada et al. | 600/547 |
| 2009/0088661 A1 | 4/2009 | Suzuki et al. | |
| 2009/0131812 A1 | 5/2009 | Sato | |

FOREIGN PATENT DOCUMENTS

| | | |
|---|---|---|
| EP | 0715829 A1 | 6/1996 |
| EP | 1512371 A1 | 3/2005 |
| EP | 1970003 A1 | 9/2008 |
| EP | 2042843 A1 | 4/2009 |
| JP | 2003052658 A | 2/2003 |
| WO | 9701303 | 1/1997 |

\* cited by examiner

*Primary Examiner* — Brian Szmal
(74) *Attorney, Agent, or Firm* — Hovey Williams LLP

(57) ABSTRACT

The present invention provides bioelectrical impedance measuring apparatus for determining composition data of the human body, the apparatus including at least eight electrodes, a pair of electrodes being assigned to each of four limbs, measuring circuitry having current sources and current and voltage measuring circuitry which may selectively be coupled to the electrodes, and a control and analysis unit which is arranged to apply, according to a plurality of predetermined measuring programs, current to two electrodes and to determine the resulting voltages with two other electrodes on different limbs and to determine the impedance of body segments based thereon. The control and analysis unit is further arranged to determine, in an advance measurement by applying current via two electrodes and measuring the resulting current through the applying electrodes and/or voltages on the other electrodes, which electrodes have contact, and to select, on the basis of the determined configuration of electrodes with contact, such matching measuring programs, in which matching measuring programs only electrodes are used for current application and voltage measurement which are contained in the determined configuration of electrodes having contact.

6 Claims, 1 Drawing Sheet

APPARATUS AND METHOD FOR BIOELECTRICAL IMPEDANCE MEASUREMENTS

CROSS-REFERENCE TO RELATED APPLICATION

Figure 1:
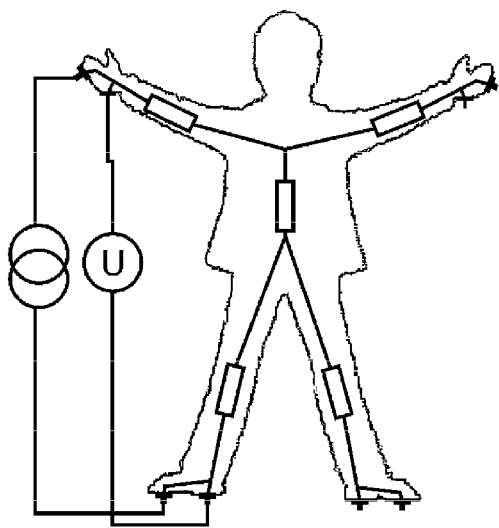

The present application claims the benefit of and priority from European Patent Application Serial No. EP 09171972.4, filed Oct. 1, 2009, the entire disclosure of which is hereby incorporated by reference herein.

BACKGROUND OF THE INVENTION

1. Field of the Invention

The present invention relates to an apparatus for bioelectrical impedance measurements for determining body composition data of the human body and to a corresponding method.

2. Discussion of the Prior Art

The conductivity of a human body is strongly influenced by its water content. Since areas of the body which are free of fat, such as muscles and bodily fluids, contain the major part of the water content of the body, while on the other hand fat tissue has a relatively low water content, the determination of the conductivity of a body or of a body segment (or the determination of the reciprocal resistance or impedance of the body or of the body segment) allows to draw conclusions on the relative fat content, at least if further data such as body height and weight of the person are taken into account.

A method and an apparatus for bioelectrical impedance analysis are described for example in WO 97/01303. The apparatus described therein comprises eight electrodes, namely four electrodes for the feet, in each case two electrodes for contacting one foot, and four hand electrodes, in each case two electrodes for contacting one hand of the person. An alternating current is applied through two electrodes which are positioned on different limbs, and the voltage between two other electrodes is measured, which measuring electrodes are likewise positioned on different limbs. By switching over to two other current applying electrodes and voltage measuring electrodes different body segments can be examined consecutively. Furthermore, when current is injected in one hand and in one foot, and voltage is measured between the other electrode on the same hand and the other electrode on the same foot, one side of the body as a whole can be measured.

If all electrodes on hands and feet are in electrical contact with their respective body member, a plurality of measuring programs or configurations is available, namely configurations as to which electrodes act as current applying electrodes and which act as voltage measuring electrodes. These configurations of current applying electrodes and voltage measuring electrodes determine which body segments is measured or whether the body as a whole is measured. If two electrodes are in electrical contact on each of the four limbs, a number of possible measuring programs is available. If electrodes are used which are attached by adhesive means there may be cases in which certain measuring programs are omitted if this allows to use fewer electrodes. In addition there are situations in which the person to be examined can not have all four limbs in contact with electrodes, for example if one limb is amputated or is covered by a dressing or plaster cast. In such situation the person to be examined will establish contact with the measuring apparatus with those limbs which are available for contacting the electrodes. Then the person to be examined or assisting personnel has to select the measuring program that is to be carried out. As mentioned above this may include, depending on the number of contact points, one or more possible measuring programs.

In EP 2 042 843 A1 it was proposed to arrange a bioelectrical impedance measuring apparatus in such a manner that the bioelectrical impedance measuring unit is switched on if it is found that at least two electrodes of the apparatus are in contact with the person to be examined, or is otherwise turned off if less than two electrodes are found to be in contact.

SUMMARY

It is an object of the present invention to arrange an apparatus for bioelectrical impedance measurement having at least eight electrodes for pairwise contact on four limbs of a person to be examined in such a manner that it may be efficiently used and easily operated by the person to be examined or by assisting personnel.

This object is solved by a bioelectrical impedance measuring apparatus including electrodes assigned to limbs of a human body, measuring circuitry selectively coupled to the electrodes, and a control and analysis unit configured to apply, according to a plurality of predetermined measuring programs, current to electrodes specific for a selected one of the particular measuring programs. In addition, a method for bioelectrical impedance measurement including assigning electrodes to limbs of the body, applying current in accordance with a plurality of predetermined measuring programs via electrodes specific for the respective measuring program, performing an advance measurement before the start of a measuring program, and selecting a measuring program based on the determined configuration of electrodes is also disclosed. Preferred embodiments are also provided.

The bioelectrical impedance measuring apparatus according to the invention has a control and analysis unit which is adapted to perform an advance measurement and to determine in that course which electrodes are in contact with the body. The control and analysis unit is further adapted, after determination of the configuration of electrodes having contact, to select from the plurality of pre-programmed and stored measuring programs those which fit to the configuration of electrodes having contact, i.e. measuring programs which utilize only those electrodes for current application and voltage measurement which are contained in the determined configuration. Whether electrodes are in contact with the body is determined by applying current through two electrodes and by sensing the resulting current through the current applying electrodes and/or the voltages on the remaining electrodes. The electrode is determined to have contact if the measured values are within predetermined limits. The current applied in advance may be an alternating current or a direct current. Furthermore, the control and analysis unit is arranged, if it is determined in the advance measurement that eight electrodes are in contact, two for each limb, to carry out executable measuring programs for measuring the impedance of each body half, each arm, each leg and of the torso.

The control and analysis unit may be arranged that the advance measurement has to be initiated by the user or is started automatically as soon as it is found that at least two electrodes are in contact.

This summary is provided to introduce a selection of concepts in a simplified form that are further described below in the detailed description of the preferred embodiments. This summary is not intended to identify key features or essential features of the claimed subject matter, nor is it intended to be used to limit the scope of the claimed subject matter.

Various other aspects and advantages of the present invention will be apparent from the following detailed description of the preferred embodiments and the accompanying drawing figures.

BRIEF DESCRIPTION OF THE DRAWING FIGURES

Figure 2:
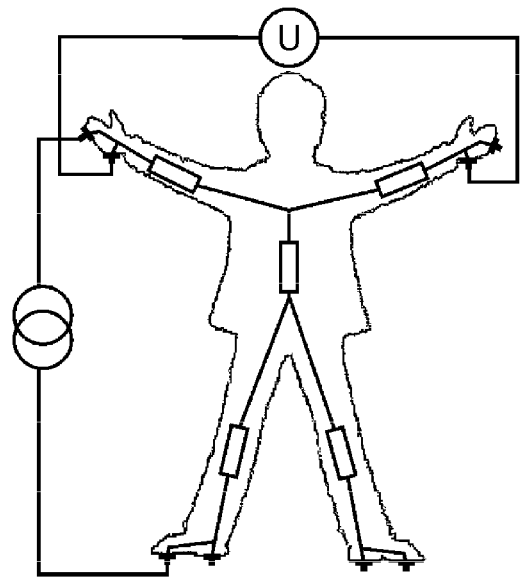
Figure 3:
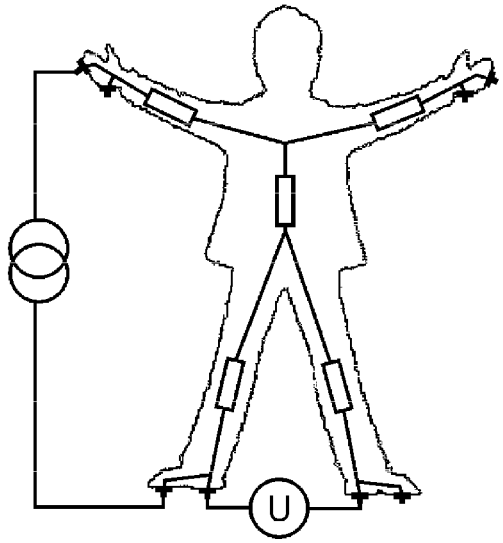
Figure 4:
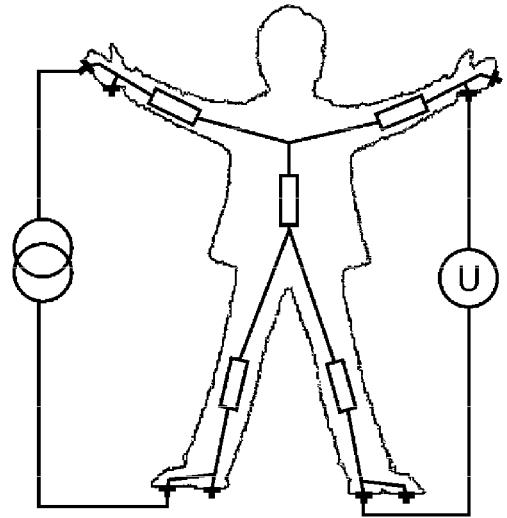

The invention is in the following described in detail in connection with preferred embodiments in the drawings in which:

FIG. 1 is a schematical block diagram for performing a first measuring program for measuring the impedance of a side of a body, FIG. 2 shows a schematical block diagram of a second measuring program for measuring the impedance of an arm, FIG. 3 shows a schematical block diagram of a third measuring program by which the impedance of a leg may be measured, and FIG. 4 shows a schematical block diagram of a forth measuring program by which the impedance of the torso is measured.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

A typical bioelectrical impedance measuring apparatus comprises a standing platform on which the person to be measured stands with both feet. For each foot two electrodes are formed on the platform, for example one in the area of the heel and one in the area of the forefoot. Furthermore, two handgrips are provided which are grasped by the user in a particular manner, thereby establishing contact with two electrodes for each hand, for example one at the thumb and the other at the palm.

According to the invention the control and analysis unit of the bioelectrical impedance measuring apparatus is arranged to perform an advance measurement during which it is determined which of the electrodes are in electrical contact with the person to be measured. For this purpose two electrodes on different limbs may for example be selected successively, and a current may be applied to these two electrodes (in the advance measurement the current may be an alternating current or a direct current), wherein the current flowing through these electrodes is measured and it is determined that the two electrodes have contact if the measured current is within predetermined current limits. This procedure is performed for further electrode pairs consecutively until it has been determined for each of the electrodes whether it has contact or not. Alternatively current is applied via two electrodes and the resulting voltage difference between two other electrodes is measured, and for these other two electrodes it is determined that they have contact if the measured voltage difference is within predetermined voltage limits.

For example, if it has been determined that eight electrodes have contact, two for each of the four limbs, a number of possible measuring programs is available, for example the measuring program illustrated in FIG. 1 in which an alternating current is applied through electrodes on one hand and one foot on the same side of the body and in which the resulting voltage is measured by the respective other electrodes of the same hand and foot. This measuring program is sensitive for the impedance of the whole body side, i.e. it provides a measure for the whole body impedance.

In the measuring program illustrated in FIG. 2 again an alternating current is applied through one electrode on a hand and one electrode on a foot on the same side of the body, and the voltage difference between the other electrode on the same hand and an electrode on the other hand is measured. This impedance measurement is sensitive for the impedance of the arm through which the current is flowing.

In the measuring program illustrated in FIG. 3 an alternating current is applied in the same manner as before and the voltage difference between an electrode on one foot and an electrode on the other foot is measured. This impedance measurement is sensitive for the impedance of the leg through which the current is flowing.

In the measuring program illustrated in FIG. 4 an alternating current is applied in the same manner as before and the voltage difference between one electrode on the hand and one electrode on the foot on the opposite side of the body is measured. This impedance measurement is sensitive for the impedance of the torso.

If it is determined in the advance measurement that eight measuring electrodes have contact, namely two electrodes for each of the limbs, all measuring programs as shown in FIG. 1-4 (and permutations thereof, i.e. permutations over the limbs) are available and are, after performance of the advance measurement, selected and provided as executable, for example as alternatives on a display, from which the user then may select, or all measuring programs are carried out.

If it is determined in the advance measurement that the electrodes of one hand have no contact, the control and analysis unit selects such measuring programs only which fit to the configuration of electrodes having contact. From the examples in FIG. 1-4 this would be the measuring programs of FIG. 1 and FIG. 3 in this case. These measuring programs are then selected and provided as executable.

If it is determined in the advance measurement that for example only the electrodes on one hand and one foot on the same side of the body have contact, the only matching measuring program of FIG. 1 is selected and provided as executable.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and access the reasonably fair scope of the present invention as pertains to any apparatus not materially departing from but outside the literal scope of the invention set forth in the following claims.

What is claimed is:

1. Bioelectrical impedance measuring apparatus for determining composition data of the human body, said apparatus comprising:

at least eight electrodes, with a pair of said electrodes being assigned to each of four limbs of the human body;

measuring circuitry including current sources and current and voltage measuring circuitry selectively coupled to the electrodes; and a control and analysis unit configured to apply, according to a plurality of predetermined measuring programs, current to two electrodes specific for a selected one of the particular measuring programs, from the current sources to the body, said control and analysis unit being further configured to determine the resulting voltages with two other specific electrodes on different limbs by means of the voltage measuring circuitry and to determine the impedance of body segments based thereon, said control and analysis unit being further configured to determine, in an advance measurement by applying current via two electrodes and measuring the resulting current through the applying electrodes and/or voltages on the other electrodes, which electrodes have contact and, if not all electrodes were found to have contact, to select, on the basis of the determined configuration of electrodes with contact, such matching ones of the predetermined measuring programs, in which matching measuring programs only use electrodes for current application and voltage measurement contained in the determined configuration of electrodes having contact, said control and analysis unit being further configured to execute, if it is determined in the advance measurement that eight electrodes have contact, two for each of the limbs, available measuring programs for measuring of the impedance of each side of the body, of each arm, of each leg, and of the torso.

2. Bioelectrical impedance measuring apparatus according to claim 1, said control and analysis unit being further configured to apply current via two electrodes in the advance measurement and to sense the current through said two electrodes and to determine that said electrodes have contact if the sensed current is within predetermined current limits.

3. Bioelectrical impedance measuring apparatus according to claim 2, said control and analysis unit being further configured to apply current via more than two electrodes in the advance measurement by applying current consecutively via different combinations of two electrodes each time, to sense the current each time and to determine that these electrodes have contact if the sensed current is within predetermined current limits.

4. Bioelectrical impedance measuring apparatus according to claim 1, said control and analysis unit being further configured to apply current via at least two electrodes in the advance measurement and to sense with two other electrodes the voltage drop over the concerned body portion between the latter electrodes, wherein said electrodes are selected for current application for which, when applying and measuring the current through said electrodes, the currents were within the predetermined limits, wherein the sensed voltage drops are checked and it is determined that the electrodes sensing the voltage drop have contact if the sensed voltage drops are within predetermined voltage limits.

5. Bioelectrical impedance measuring apparatus according to claim 1, said control and analysis unit further configured to display, if after the advance measurement a plurality of measuring programs match the determined configuration of electrodes having a contact, the selected measuring programs on a display.

6. Method for bioelectrical impedance measurement for determining composition data of a human body, said method comprising the steps of:

assigning two electrodes to each of the limbs of the body;

applying an alternating current in accordance with a plurality of predetermined measuring programs via two electrodes specific for the respective measuring program and, with two specific electrodes on different limbs, the resulting voltage is sensed and the impedance of that body segment is determined for which body segment the measuring program is specific;

performing an advance measurement before the start of a measuring program by applying consecutively, via different electrode pairs, a current and by measuring the resulting current through the applying electrodes and/or the voltages at the remaining electrodes, in order to determine, for those electrodes for which the measuring values are within predetermined limits, that they have contact;

if not all electrodes were found to have contact, selecting, based on the determined configuration of electrodes having contact, measuring programs matching this configuration, in which measuring programs only electrodes designated for current application and voltage measurement are contained in the determined configuration; and if it is determined in the advance measurement that eight electrodes have contact, two for each limb, carrying out executable measuring programs for these eight electrodes for measuring the impedance of each side of the body, of each arm, of each leg, and of the torso.

* * * * *